United States Patent [19]

Gunkel

[11] Patent Number: 4,575,563

[45] Date of Patent: Mar. 11, 1986

[54] LIQUID MIXTURES OF TRIALKYLPHOSPHINE OXIDES

[75] Inventor: Louis T. Gunkel, Yardley, Pa.

[73] Assignee: FMC Corporation, Philadelphia, Pa.

[21] Appl. No.: 575,734

[22] Filed: Feb. 1, 1984

[51] Int. Cl.$^4$ ................................. C07F 9/53
[52] U.S. Cl. ................................. 568/14; 523/506; 524/912
[58] Field of Search ........................ 568/14

[56] References Cited

U.S. PATENT DOCUMENTS

| | | | |
|---|---|---|---|
| 3,304,330 | 2/1967 | Yoke | 568/14 |
| 3,309,408 | 3/1967 | Moedritzer | 568/14 |
| 3,520,939 | 7/1970 | Brennan | 568/14 |
| 3,657,352 | 4/1972 | Kleiner | 568/14 |
| 3,709,852 | 1/1973 | Gordon et al. | 260/88.2 S |
| 4,452,716 | 6/1984 | Cummins et al. | 568/14 |

FOREIGN PATENT DOCUMENTS 1298386  11/1972  United Kingdom ................ 568/14

*Primary Examiner*—Helen M. S. Sneed
*Attorney, Agent, or Firm*—Robert D. Jackson; Eugene G. Horsky

[57] ABSTRACT

Liquid mixtures of trialkylphosphine oxides, useful as antistats in thermoplastic polymers, are obtained by alkylating excess phosphine with a mixture of higher α-olefins to give a mixture of higher alkylated phosphines and unreacted phosphine and alkylating that mixture with a lower α-olefin. This method provides a larger percentage of higher alkyl groups and a lower percentage of lower alkyl groups compared to alkylating the phosphine with all of the mixed α-olefins in a single reaction. The shift in higher alkyl groups decreases the volatility of the trialkylphosphine mixture and is an advantage when preparing plastic compositions at higher formulation temperatures.

6 Claims, 1 Drawing Figure

DISTRIBUTION OF ALKYL GROUPS IN LIQUID MIXTURES OF TRIALKYL PHOSPHINE OXIDES (DHOPO)
D = DECYL
H = HEXYL
O = OCTYL
 
| TRIALKYL GROUPING | STATISTICAL DISTRIBUTION OF D, H AND O GROUPS | INCREASED DISTRIBUTION OF O AND D GROUPS |
|---|---|---|
| HHH | 2.85 | 1.45 |
| HHO | 9.12 | 2.01 |
| HHO+HHD | 19.38 | 4.45 |
| HOD+OOO | 24.32 | 14.54 |
| HDD+OOD | 22.36 | 32.32 |
| ODD | 11.81 | 31.05 |
| DDD | 4.0 | 10.29 |
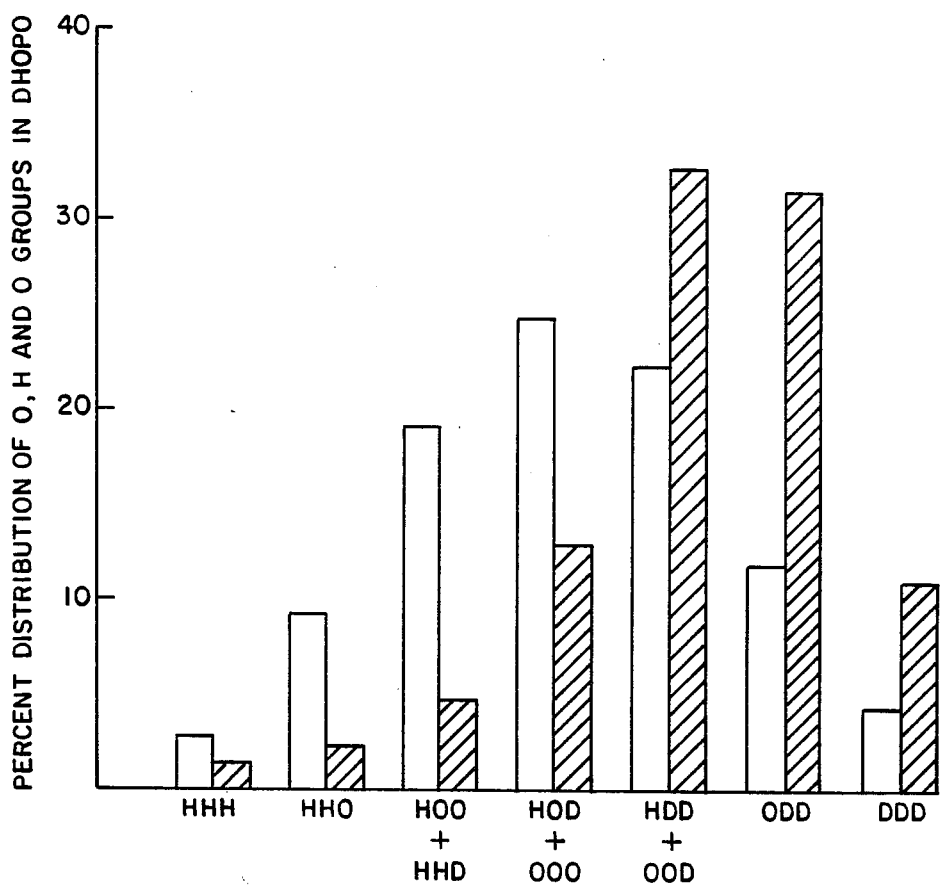

LIQUID MIXTURES OF TRIALKYLPHOSPHINE OXIDES

This invention relates to trialkylphosphine oxides, and in particular to liquid mixtures thereof, useful as antistatic agents for thermoplastic polymers.

In pending application Ser. No. 512,286 filed on July 8, 1983, now U.S. Pat. No. 4,552,687, by Beacham et al, there is disclosed a class of liquid mixtures of trialkylphosphine oxides which, on being incorporated into a thermoplastic polymer, increase its electrical conductivity thereby reducing the polymer's susceptibility to static charge build up. It had previously been known from U.S. Pat. No. 3,709,852 to Gordon et al that trialkylphosphine oxides acted as antistatic agents in thermoplastic polymer. However, Gordon et al employed their trialkylphosphine oxides in the form of solid powders which were considerably less effective as antistats than the liquid trialkylphosphine oxides of the aforesaid application.

The electrical conductivity of thermoplastic polymers containing trialkylphosphine oxides is thought to involve oxidation of the phosphine oxide molecules in an electrical field thereby providing paths of alternating semi polar bonds. Apparently, such a mechanism is favored when using the liquid phosphine oxides which are dissolved rather than suspended as particulate solids in the polymer matrix. This would account for the superior antistatic properties of the polymer compositions of the application over those of the cited patent.

Trialkylphosphine oxides as a class, are low melting, highly crystalline solids. To obtain liquid products, individual members are blended together to provide mixtures which through mutual melting point depression tend to remain in the liquid state at room temperature. However, this procedure can be laborious and time-consuming owing to the number of components needed to ensure against crystallization. An improved technique for realizing liquid mixtures of trialkylphosphine oxides is described in the Beacham et al application. This is implemented by simultaneously reacting, under free radical conditions, phosphine with different α- or 1-olefins followed by oxidation of the reaction product as shown in the following scheme:

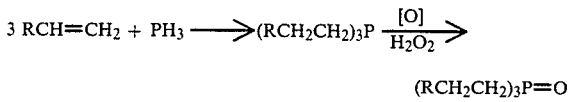

$$3\ RCH{=}CH_2 + PH_3 \longrightarrow (RCH_2CH_2)_3P \xrightarrow[H_2O_2]{[O]}$$

$$(RCH_2CH_2)_3P{=}O$$

wherein R is alkyl of 1 to 16 carbon atoms in a mixture of α-olefins. This approach results in a normal statistical distribution of all possible trialkylphosphine oxide configurations thereby providing a reaction product which is resistant to crystallization by virtue of mutual melting point depression of its numerous components. Thus for instance, by reacting one mole of phosphine with an equimolar quantity each of 1-hexene, 1-octene and 1-decene as above described, there is obtained a trialkylphosphine oxide mixture made up of all possible combinations of hexyl, octyl and decyl groups attached to the phosphorus atom. An analysis of the mixture shows it to consist of a statistical distribution of trialkylphosphine oxides in which the percent of trihexyl and tridecyl members are at opposite ends of a Gaussian or bell curve while the percent of mixed alkyl members fall in the upper regions of the curve.

Although polymer compositions containing mixtures of trialkylphosphine oxides prepared in the aforesaid manner exhibit excellent antistatic behavior, certain problems have been encountered when working with higher melting thermoplastic polymers such as nylon. Specifically, the formulation temperature is so high that some of the lower boiling trialkylphosphine oxides may be lost because of vaporization. This can decrease the tendency of the trialkylphosphine oxide mixture to remain liquid with risk of crystallization and concomitant diminution of antistatic properties. Further, volatilization of the phosphine oxide additive gives rise to excessive fuming and may even present a fire hazard.

In accordance with the present invention, it has been discovered that the seriousness of the problems aforesaid can be greatly diminished when preparing the liquid mixed trialkylphosphine oxide by first reacting, in the presence of a free radical catalyst, phosphine with the higher molecular weight α-olefins wherein some of the hydrogen atoms in the phosphine is replaced with alkyls derived from the higher molecular weight α-olefins followed by subsequent introduction of a lower molecular weight α-olefin and continuing the reaction until the remainder of the hydrogen on the phosphines have been replaced by the lower molecular weight alkyl derived from the lower molecular weight α-olefin. The mixed trialkylphosphines are then oxidized to give liquid mixed trialkylphosphine oxides. This gives rise to a skewing of the normal distribution of the trialkylphosphine oxide mixture with the percent of trialkyl component being elevated while the percent of the lowest trialkyl component is diminished. Since the lowest trialkylphosphine oxide possesses the lowest boiling point, its suppression in favor of the higher members results in less vaporization losses when the modified trialkylphosphine oxide mixture is incorporated into a thermoplastic polymer, particularly at higher formulation temperatures.

Reference is now made to the drawing which is a bar graph showing the percentage composition of trialkylphosphine oxide mixtures prepared by reacting phosphine with a mixture of 1-hexene, 1-octene and 1-decene and subsequent oxidation. The bell curve, defined by the white bars, depicts the normal statistical distribution of trialkylphosphine oxides obtained by reacting one mole of phosphine with equimolar quantities of the three different α-olefins aforesaid. As will be observed, the trihexyl and tridecylphosphine, representing the lowest and highest molecular weight members in the mixture, occur in essentially equal percentages at the extreme ends of the distribution. In the skewed curve, represented by the crosshatched bars, the percent of the trihexyl component is depressed while that of the tridecyl is correspondingly elevated. The skewed distribution is affected by first reacting phosphine with an equimolar mixture of 1-octene and 1-decene to give an alkylated phosphine in which there are at least some free phosphine hydrogens followed by introduction of one mole of 1-hexene to engender the final trialkylphosphine mixture which is then converted to the oxide.

That the normal distribution of trialkylphosphine oxides in mixtures thereof could be altered by sequentially reacting phosphine with α-olefins as described herein is indeed surprising. It would be expected that primarily trisubstituted phosphines would be produced in the first step owing to the greater reactivity of the hydrogen atoms in the initially formed mono- and dialkylphosphines. Even with a large excess of phosphine, the olefins would be expected to react with the increasingly activated mono- and dialkylphosphines leaving the less reactive phosphine untouched. No explanation is presently known which would account for such behavior.

In carrying out the invention herein, liquid mixtures of trialkylphosphine oxides having a decreased percentage of the lowest boiling members and a corresponding increased percentage of the highest boiling members are obtained by first reacting equimolar proportions of the corresponding higher α-olefins with sufficient phosphine to give a first reaction mixture containing mono- and disubstituted phosphines and free phosphine which is then reacted with the corresponding lower α-olefin. The reaction is conducted under free radical producing conditions. After completion, excess α-olefins and any solvent is distilled off and the residual trialkylphosphines oxidized to give liquid mixture of trialkylphosphine oxides.

In general, the liquid trialkylphosphine oxides of the invention will be a three component system formed by reacting, in the presence of a free radical catalyst, phosphine with 2 moles each of two higher molecular weight α-olefins followed by reacting with 1 mole of the lower molecular weight α-olefin. In each case, the reaction is continued until the α-olefins are essentially depleted. Reaction conditions are generally in the temperature range of about 100° C. to about 150° C., preferably about 115° C. to 120° C. A sealed reaction vessel is desirable, with starting pressures at about 150 to 250 psi, typically about 200 psi. The reaction media can be any relatively inert, liquid organic solvent such as liquid aromatic hydrocarbons, for instance benzene, toluene and xylene, preferably toluene. After all of the α-olefins have been reacted, the solvent and other volatiles are distilled off and the residue of trialkylphosphines subjected to oxidation, preferably using hydrogen peroxide as the oxidant. Especially preferred mixed trialkylphosphine oxides herein are those in which the alkyls are hexyl, octyl and decyl. These are prepared in the presence of a free catalyst, by reacting 1 mole of phosphine with 2 moles each of 1-octene and 1-decene followed by adding 1-hexene to the completed first reaction mixture to give a trialkylphosphine in which the alkyls are permutations and combinations of hexyl, octyl and decyl. The trialkylated phosphine mixture is oxidized with hydrogen peroxide to give a liquid mixture of the corresponding phosphine oxides in which there is a lower percent of the trihexyl member and a percentage of the higher tridecyl member.

Exemplary polymers which can be rendered electrically conductive by treatment with the herein liquid trialkylphosphine oxides are of the thermoplastic type such as polyethylene, polypropylene, polybutene, polypentene, polyhexene and other poly α-olefins and copolymers of ethylene with α-olefins; polyamides, polystyrene, polymeric esters, for example, polymethacrylates and the like. The antistatic plastic compositions of the invention may contain other adjuncts familiar in the art of plastic formulation such as stabilizers, lubricants, nucleating agents, plasticizers, fillers, pigments and other processing components.

The novel electrically conducting polymers of the invention afford excellent protection against static electricity to meet a variety of situations and conditions. These include accumulation of dust and dirt from electrostatic attraction; unpleasant shocks to personnel and handling problems such as can occur during windup of highly charged film or when static material has a tendency to stick to metal parts. Perhaps nowhere is the problem of static electricity more acute than in the electronics industry where increased microminiaturization of components makes them extremely vulnerable to damage from even relatively low voltage discharges, as low as 100 to 200 volts, for example. It is estimated that the electronics industry sustained at least 500 million dollars of damage in 1981 from ruined equipment due to static electricity. Since the antistatic plastic composition herein can be formulated to give conductivities as low as $10^8$ ohms·cm, they are particularly useful in protecting delicate microcircuitry against damage from low voltage which requires greater conductivity for its removal.

In addition to their antistatic properties, the mixed liquid trialkylphosphine oxides of the invention possess other useful and valuable characteristics. For instance, liquid decyl hexyl octylphosphine oxide, a representative member of the series obtained by reacting molar proportions of 1-hexene, 1-octene and 1-decene with phosphine followed by oxidation of the reaction mixture, is capable of plasticizing nylon. This is indeed surprising in view of nylon's inertness and incompatibility with the normally used plasticizers. Even more surprising, however, are the properties of nylon plasticized with the herein liquid trialkylphosphine oxide. Particularly noteworthy in this regard is the unusually high luster of fibers spun from these novel plasticized nylon compositions. Dyed fabrics manufactured from such transparent fibers should, therefore, exhibit much greater color brightness compared with conventional nylon textiles. Another surprising and further unexpected property of the herein plasticized nylon is that during cold drawing, the resulting fibers become increasingly more extendable without any apparent loss of tensile strength. Normally, incorporation of a plasticizer in a polymer causes a decrease—not an increase in physical strength.

Plastic films containing the liquid trialkylphosphine oxides of the invention are rendered more transparent. For example, polyethylene film, which tends to be milky or hazy, was obtained in highly clarified form. Similar results were realized with nylon film.

It is believed that the presence of the herein mixed liquid trialkylphosphine oxides in the plastic promotes alignment of the polymer chains thereby increasing the crystallinity of oriented plastic materials. This could account for their enhanced clarity and fiber strength. However, it is to be understood that the foregoing is offered by way of an explanation and is not to be taken as limiting the invention.

The quantity of liquid trialkylphosphine oxide incorporated in the polymer is not especially critical although it will be appreciated that excessively large amounts above that needed to achieve the desired antistatic effect or other properties should be avoided. In general, the limiting quantity will be that below which blooming of the additive occurs on the surface of the plastic substrate. When used as an antistatic agent, the amount required is inversely proportional to the voltage to be discharged, that is, low voltages require larger additions than high voltages. Normally, the plastic compositions of the invention will contain from about 0.1% to about 20% of the phosphine oxide based on the weight of the polymer. Dissipation of low voltages generally requires high percentages, approaching 20%. To realize fiber lustrousness, on the other hand, or film clarity, relatively minute amounts will suffice, on the order of 0.1%.

Minimum quantities of phosphine oxide required will depend not only on the level of static dissipation desired but the polymer system to be treated. Included in the latter should be the effects of all other components. Polyethylene, which in commercial materials normally contains minimum or no interfering additions, can be rendered highly capable of electrostatic discharge with about 1.0 parts phosphine oxide per hundred of resin. In contrast, polypropylene, which must be modified with an antioxidant stabilizer, normally requires higher levels to achieve the same performance. The reasons for this are not entirely understood but it is believed that most phenolic type antioxidants interact by hydrogen-bonding with the phosphine oxide, reducing its capability to associate in a conducting mode.

The upper limit of effectiveness is determined principally by the extent to which the phosphine oxide is compatible with the polymers. Rate of static discharge increases with increasing concentrations of additive until the level is reached at which surface "blooming" occurs. Higher levels then show no further increases.

That the discharge mechanism is volume related rather than limited to surface effects, is illustrated by using polypropylene which is highly compatible with the phosphine oxides. Here both sheet resistance and volume resistivity as well as the desired static dissipation time continue to decrease as the amount of phosphine oxide increases. This is in contrast with the commercial surface action electrostatic treatments where sheet resistance and static discharge time may decrease with increases in the amount of additive but the volume resistance is unaffected.

Further evidence that the phosphine oxides exert their influence in the interior of the polymer is found in the changes which occur in physical properties and appearance. When polyethylene film is produced, distension during blowing approximately doubles when the phosphine oxide is present, indicating an increase in melt fluidity. Furthermore, the film acquires an enhanced transparency and sparkle. In the case of nylon crystallinity, as determined by microcolorimetry, it is reduced by one-fourth to one-half in molded specimens. The extensibility of nylon fibers is approximately doubled at no sacrifice in tensile strength while luster is greatly increased, giving the appearance of natural silk.

Reference is made to the following examples.

EXAMPLE I

This Example describes the single addition reaction of 1 mole of phosphine with a mixture of 1 mole each of 1-hexene, 1-octene and 1-decene to give a trialkylphosphine consisting of hexyl, octyl and decyl groups followed by oxidation with hydrogen peroxide. The product consists of a normal distribution of the trisubstituted phosphine oxides as represented by the white bar graph of the drawing.

In carrying out this Example, 4847 g. of 1-hexene (57.5 moles), 6456 g. of 1-octene (57.5 moles) and 8081 g. of 1-decene (57.6 moles) were placed in a 10-gallon pressure autoclave made of 316 stainless steel and the temperature brought to 115° C. One thousand nine hundred grams of phosphine (55.8 moles) were introduced into the reactor, which was then sealed and heated to 115° C.

A solution of 50 g. of azobisisobutyronitrile in 1750 g. of toluene was added to the pressure reactor over a six-hour period during which the pressure dropped from 200 psi to 40 psi.

The reactor was cooled down and the product mixture was stripped of solvent and excess olefins under vacuum. Eighteen thousand five hundred fifty grams of hexyl octyl decyl phosphine were removed. This material was then oxidized with 6150 grams of 30% $H_2O_2$ (54.2 moles). The yield of product following removal of water from the oxidation reaction was 19000 grams (49.1 moles).

There was obtained a normal statistical distribution of the resulting trialkylphosphine oxides, the percentages of which are as follows:

| | |
|---|---|
| HHH | 2.60 |
| HHO | 9.00 |
| HOO + HHD | 19.60 |
| HOD + OOO | 25.00 |
| HDD + OOD | 22.80 |
| ODD | 12.20 |
| DDD | 4.10 |

H = decyl;
O = octyl;
D = decyl.

EXAMPLE II

This is an Example of preparing a skewed trialkylphosphine oxide mixture in which the percentage of lower alkyls is suppressed and the percentage of higher alkyls is elevated. The skewed composition is defined by the cross-hatched bar graph of the drawing.

Into a 2-liter autoclave made of 316 stainless steel were placed 180 g. of 1-octene (1.6 moles) and 224 g. of 1-decene (1.6 moles) after which 51 g. of phosphine (1.5 moles) were introduced. The reactor was sealed and heated with stirring to 112° C. to 115° C. (pressure=200 psig at start). Three grams of azobisisobutyronitrile (Va$_2$O 64) dissolved in 150 ml of toluene were then prepared and 100 ml of this mixture was added to the reactor over a four-hour period. The pressure dropped to 40 psig, indicating that the phosphine was reacting.

The reaction was allowed to stand overnight (not necessary but convenient). The following morning the reactor was reheated to 112° C. to 115° C. and 151 grams of 1-hexene were pumped into the reactor via a high pressure pump (pressure=40 psig).

Eighty ml of the catalyst solution previously prepared was then added to the reactor over a three-hour period. The pressure dropped to 30 psig and held there due to toluene at 115° C. in the reactor.

The reactor was cooled down and the contents removed and stripped of solvent (toluene and excess olefins). A weight of 432 g. of mixed hexyl octyl decyl phosphine was obtained. The mixture was oxidized with 143 g. of 30% $H_2O_2$ (1.26 moles) to yield 452 g. of the phosphine oxide (1.2 moles).

The distribution of the alkyl phosphine oxide in the product is given below:

| | |
|---|---|
| HHH | 1.45 |
| HHO | 2.01 |
| HOO + HHD | 4.45 |
| HOD + OOO | 14.54 |
| HDD + OOD | 32.32 |
| ODD | 31.05 |
| DDD | 10.29 |

As can be seen, the skewed distribution shows a lower percentage of the trihexylphosphine oxide and a corresponding increase in the percentage of the tridecylphosphine oxide. As a consequence, there is less volatilization of the skewed trialkylphosphine during formulation of plastic compositions.

What is claimed is:

1. In a process of producing liquid mixtures of trialkylphosphine oxides by alkylating phosphine with a mixture of α-olefins in the presence of a free radical source and oxidizing the resulting trialkylphosphine mixture; the improvement of decreasing the volatility of the trialkylphosphine oxide mixture by increasing therein the ratio of higher trialkyl groups to lower trialkyl groups and oxidizing the trialkylphosphine mixture, comprising:

a. forming an initial reaction mixture of alkylated phosphines containing the higher alkyl groups and unreacted phosphine by alkylating excess phosphine with a mixture of the corresponding higher α-olefins;

b. forming a final reaction mixture of trialkylphosphines by alkylating the initial reaction mixture with a lower α-olefin, and c. oxidizing the reaction mixture of step b. to the corresponding mixture of trialkylphosphine oxides.

2. The process according to claim 1 wherein the trialkyl groups are derived from three different α-olefins.

3. The process according to claim 2 wherein the α-olefins are selected from the class consisting of 1-hexene, 1-octene and 1-decene.

4. The product of the process of claim 1.

5. The product of the process of claim 2.

6. The product of the process of claim 3.

* * * * *